United States Patent
Aoyama

(10) Patent No.: US 10,335,014 B2
(45) Date of Patent: Jul. 2, 2019

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Tatsuya Aoyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 357 days.

(21) Appl. No.: 14/672,393

(22) Filed: Mar. 30, 2015

(65) Prior Publication Data

US 2015/0272422 A1 Oct. 1, 2015

(30) Foreign Application Priority Data

Mar. 31, 2014 (JP) ................................. 2014-074275

(51) Int. Cl.
*A61B 1/00* (2006.01)
*A61B 1/06* (2006.01)
(Continued)

(52) U.S. Cl.
CPC ...... *A61B 1/00006* (2013.01); *A61B 1/00009* (2013.01); *A61B 1/045* (2013.01);
(Continued)

(58) Field of Classification Search
CPC . A61B 1/00006; A61B 1/00009; A61B 1/045; A61B 1/0638; G01B 11/14; H04N 5/2256
(Continued)

(56) References Cited

U.S. PATENT DOCUMENTS 5,218,414 A * 6/1993 Kajiwara ................ G01S 11/12
356/3
6,115,554 A * 9/2000 Ito ............................ G02B 7/32
396/106
(Continued)

FOREIGN PATENT DOCUMENTS

EP 1241896 A2 9/2002
EP 2371267 A1 * 10/2011 ............. A61B 1/043
(Continued)

OTHER PUBLICATIONS

Japanese Office Action, dated Apr. 13, 2016, for Japanese Application No. 2014-074275 along with an English machine translation.
(Continued)

*Primary Examiner* — Richard A Hansell, Jr.
(74) *Attorney, Agent, or Firm* — Birch, Stewart, Koalsch & Birch, LLP

(57) ABSTRACT

An endoscope system comprises an LED light source unit, an image sensor, an imaging distance calculator and a light source controller. The LED light source unit generates illumination light. The image sensor has a blue pixel, a green pixel, a red pixel and a specific pixel receiving at least light in a blue wavelength band and a green wavelength light, and images an observation object by reflected light of the illumination light from the observation object. The imaging distance calculator calculates an imaging distance that is a distance between the image sensor and the observation object. The light source controller controls the light source unit to increase a component of the blue wavelength band or the green wavelength band included in the illumination light according to the imaging distance.

13 Claims, 14 Drawing Sheets

(51) Int. Cl.
*H04N 9/04* (2006.01)
*A61B 1/045* (2006.01)
*G01B 11/14* (2006.01)
*H04N 5/225* (2006.01)

(52) U.S. Cl.
CPC .......... *A61B 1/0638* (2013.01); *A61B 1/0661* (2013.01); *G01B 11/14* (2013.01); *H04N 5/2256* (2013.01); *H04N 9/045* (2013.01); *H04N 2005/2255* (2013.01)

(58) Field of Classification Search
USPC .......................................................... 348/68
See application file for complete search history.

(56) References Cited

U.S. PATENT DOCUMENTS

| | | | | |
|---|---|---|---|---|
| 8,594,465 | B2* | 11/2013 | Karlov | G06T 3/4007 382/162 |
| 9,699,429 | B2* | 7/2017 | Kaizu | H04N 9/07 |
| 2005/0084147 | A1* | 4/2005 | Groszmann | A61B 6/4441 382/131 |
| 2006/0215406 | A1* | 9/2006 | Thrailkill | A61B 1/0676 362/249.06 |
| 2009/0014624 | A1* | 1/2009 | Blees | F21L 4/00 250/201.4 |
| 2010/0165135 | A1* | 7/2010 | Kalevo | H04N 5/2351 348/221.1 |
| 2011/0050918 | A1* | 3/2011 | Tachi | H04N 5/217 348/208.4 |
| 2011/0063427 | A1 | 3/2011 | Fengler et al. | |
| 2011/0085784 | A1* | 4/2011 | Imamura | G03B 5/02 396/55 |
| 2011/0228074 | A1* | 9/2011 | Parulski | G03B 15/05 348/81 |
| 2012/0154565 | A1 | 6/2012 | Kaku | |
| 2012/0154637 | A1* | 6/2012 | Hara | H04N 5/23212 348/239 |
| 2013/0182169 | A1* | 7/2013 | Kosugi | G02B 23/2415 348/335 |
| 2014/0180129 | A1 | 6/2014 | Kostenich et al. | |
| 2015/0103212 | A1* | 4/2015 | Saito | H04N 9/045 348/242 |
| 2016/0171651 | A1* | 6/2016 | Lee | G06T 3/4015 382/300 |
| 2016/0338166 | A1* | 11/2016 | Knaapen | H05B 33/0845 |

FOREIGN PATENT DOCUMENTS

| | | | | |
|---|---|---|---|---|
| EP | 2371267 A1 * | 10/2011 | ............. | A61B 1/043 |
| JP | 2011-36361 A | 2/2011 | | |
| JP | 2012-125462 A | 7/2012 | | |
| JP | 2013-27636 A | 2/2013 | | |
| JP | 2013-34753 A | 2/2013 | | |
| JP | 5141757 B2 | 2/2013 | | |
| JP | 2013-163027 A | 8/2013 | | |
| JP | 2014-504938 A | 2/2014 | | |
| WO | WO 2012107884 A1 * | 8/2012 | ............. | A61B 1/041 |
| WO | WO-2012107884 A1 * | 8/2012 | ............. | A61B 1/041 |

OTHER PUBLICATIONS

Extended European Search Report, dated Aug. 10, 2015, for European Application No. 15159918.0.

* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

The present application claims priority under 35 U.S.C. § 119 to Japanese Patent Application No. 2014-074275, filed Mar. 31, 2014. The above application is hereby expressly incorporated by reference, in its entirety, into the present application.

BACKGROUND OF THE INVENTION

1. Field of the Invention

The present invention relates to an endoscope system, a processor device, and a method for operating an endoscope system, for imaging an observation object in a patient.

2. Description Related to the Prior Art

In a medical field, it is common to image an observation object (for example gastrointestinal mucous membranes) in a patient, and observe the image for a diagnosis. An endoscope system comprises a light source device for generating illumination light to irradiate an observation object, an endoscope having an insertion section for being inserted in a patient and imaging the observation object with use of an image sensor provided in a distal portion of the insertion section, and a processor device for generating an image of the observation object based on image signals which the image sensor outputs and displaying the image on a monitor.

The image sensor for imaging the observation object is for example a color image sensor which includes a blue pixel (hereinafter referred to as the B pixel) for receiving light in a blue wavelength band, a green (hereinafter referred to as the G pixel) for receiving light in a green wavelength band, and a red pixel (hereinafter referred to as the R pixel) for receiving light in a red wavelength band. Recently, it is known an endoscope system using a color image sensor that includes the B pixel, G pixel, and R pixel of three primary colors, and a fourth color pixel whose spectral characteristic is different from that of the BGR pixels. For example, they are known an endoscope system equipped with a color image sensor which includes the BGR pixels, and a pixel for receiving light in a blue wavelength band which is narrower than the wavelength band of the light received by the B pixel, and an endoscope system equipped with a color image sensor which further includes a pixel for receiving light in a green wavelength band which is narrower than the wavelength band of the light received by the G pixel (United States Patent Application Publication No. 2012/154565 corresponding to Japanese Patent Laid-Open Publication No. 2012-125462). In addition, it is known an endoscope system which includes an image sensor having the BGR pixels and a pixel to receive near infrared light (United States Patent Application Publication No. 2011/063427 corresponding to Japanese Patent Laid-Open Publication No. 2013-163027).

Further, it is known a color image sensor that has the BGR pixels and a white color pixel (hereinafter referred to as the W pixel) which receives each light in a blue wavelength band, a green wavelength band and a red wavelength band (Japanese Patent No. 5141757). The color image sensor having the W pixel is used for digital cameras to image a person or scenery.

In case an observation object is imaged by the endoscope system, a distance between the distal portion of the insertion section where the image sensor is mounted and the observation object, that is, a distance between the image sensor and the observation object which the image sensor images (hereinafter referred to as the imaging distance) varies according to how a doctor using the endoscope system observes the observation object.

For example, in case running patterns of blood vessels or microstructures such as pit patterns on a surface (or a vicinity of a surface) of the observation object are observed, the distal portion of the insertion section is brought close to the observation object so as to greatly observe the running patterns of the blood vessels or the pit patterns. Accordingly, in case the distal portion of the insertion section is brought close to the observation object (the imaging distance is short), the endoscope system is expected to offer an image in which the running patterns of the blood vessels or the pit patterns can be easily observed.

On the other hand, for searching a lesion part, the distal portion of the insertion section is kept away from the observation object to observe digestive organs generally from a remote place. Accordingly, in case the distal portion of the insertion section is kept away from the observation object (the imaging distance is long), the endoscope system is expected to offer an image in which it is easy to discover lesions in a distant view.

SUMMARY OF THE INVENTION

An object of the present invention is to provide an endoscope system, a processor device, and a method for operating an endoscope system, which can acquire an image in which a desired structure can be easily observed according to an imaging distance.

In order to achieve the above and other objects, an endoscope system of the present invention comprises a light source device, an image sensor, an imaging distance calculator and a light source controller. The light source device generates illumination light to irradiate an observation object and is able to control an optical spectrum of the illumination light. The image sensor includes a blue pixel receiving light in a blue wavelength band, a green pixel receiving light in a green wavelength band, a red pixel receiving light in a red wavelength band, and a specific pixel receiving at least light in a blue wavelength band and a green wavelength light, and images the observation object by reflected light of the illumination light from the observation object. The imaging distance calculator calculates an imaging distance that is a distance between the image sensor and the observation object. The light source controller increases a component of the blue wavelength band or the green wavelength band included in the illumination light according to the imaging distance.

It is preferable that the light source controller increases the component of the green wavelength band included in the illumination light as the imaging distance becomes longer.

It is preferable that the light source controller increases the component of the blue wavelength band included in the illumination light as the imaging distance becomes shorter. It is more preferable that the light source controller increases the component of the blue wavelength band included in the illumination light and decreases the component of the green wavelength band included in the illumination light as the imaging distance becomes shorter. Furthermore, it is preferable that the light source controller decreases the component of the red wavelength band included in the illumination light as the imaging distance becomes shorter.

It is preferable that the endoscope system further comprises a judgment section that compares the imaging distance with a predetermined threshold value, judges that the imaging distance is short in case the imaging distance is shorter than the threshold value, and judges that the imaging distance is long in case the imaging distance is longer than the threshold value. The light source controller increases the component of the blue wavelength band or the green wavelength band included in the illumination light based on the judgment result input from the judgment section.

It is preferable that the endoscope system further comprises an exposure setting value calculator which calculates an exposure setting value to control an exposure amount when the observation object is imaged, based on image signals which the image sensor outputs. In this case, the imaging distance calculator calculates the imaging distance based on the exposure setting value.

It is preferable that the endoscope system further comprises a gain controller that controls a gain when the image sensor outputs image signals, and the imaging distance calculator calculates the imaging distance based on the gain.

It is preferable that the endoscope system further comprises an imaging optical system in which an imaging magnification is variable, and the imaging distance calculator calculates the imaging distance based on the imaging magnification.

It is preferable that the endoscope system further comprises a demosaic processor which applies a first demosaic process performed with the specific pixel working as the green pixel or a second demosaic process performed with the specific pixel working as the blue pixel, to an image signal which the image sensor outputs.

A method for operating an endoscope system of the present invention comprises an imaging distance calculation step and a light source-controlling step. The endoscope system includes a light source device which generates illumination light to irradiate an observation object and is able to control an optical spectrum of the illumination light, and an image sensor which has a blue pixel receiving light in a blue wavelength band, a green pixel receiving light in a green wavelength band, a red pixel receiving light in a red wavelength band, and a specific pixel receiving at least light in a blue wavelength band and a green wavelength light, and images the observation object by reflected light of the illumination light from the observation object. In the imaging distance calculation step, an imaging distance calculator calculates an imaging distance which is a distance between the image sensor and the observation object. In the light source-controlling step, a light source controller increases the component of the blue wavelength band or the green wavelength band included in the illumination light based on the imaging distance.

A processor device of the present invention is used for an endoscope system and comprises an imaging distance calculator and a light source controller. The endoscope system includes a light source device which generates illumination light to irradiate an observation object and is able to control an optical spectrum of the illumination light, and an image sensor which has a blue pixel receiving light in a blue wavelength band, a green pixel receiving light in a green wavelength band, a red pixel receiving light in a red wavelength band, and a specific pixel receiving at least light in a blue wavelength band and a green wavelength light, and images the observation object by reflected light of the illumination light from the observation object. The imaging distance calculator calculates an imaging distance that is a distance between the image sensor and the observation object. The light source controller increases the component of the blue wavelength band or the green wavelength band included in the illumination light based on the imaging distance.

It is preferable that the light source device includes a light source unit and a light source controller. The light source unit generates the illumination light to irradiate the observation object and is able to control an optical spectrum of the illumination light. The light source controller controls the light source unit.

It is preferable that in the light source-controlling step, the light source controller included in the light source device controls the light source unit that is included in the light source device and generates the illumination light to irradiate the observation object.

According to the endoscope system, the processor device, and the method for operating an endoscope system of the present invention, an image in which a desired structure can be easily observed can be acquired according to an imaging distance, since the observation object is imaged by the color image sensor which has the blue, green and red pixels and the specific pixel receiving at least light in a blue wavelength band and a green wavelength light, and the component of the blue wavelength band or the green wavelength band included in the illumination light is increased based on the imaging distance.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
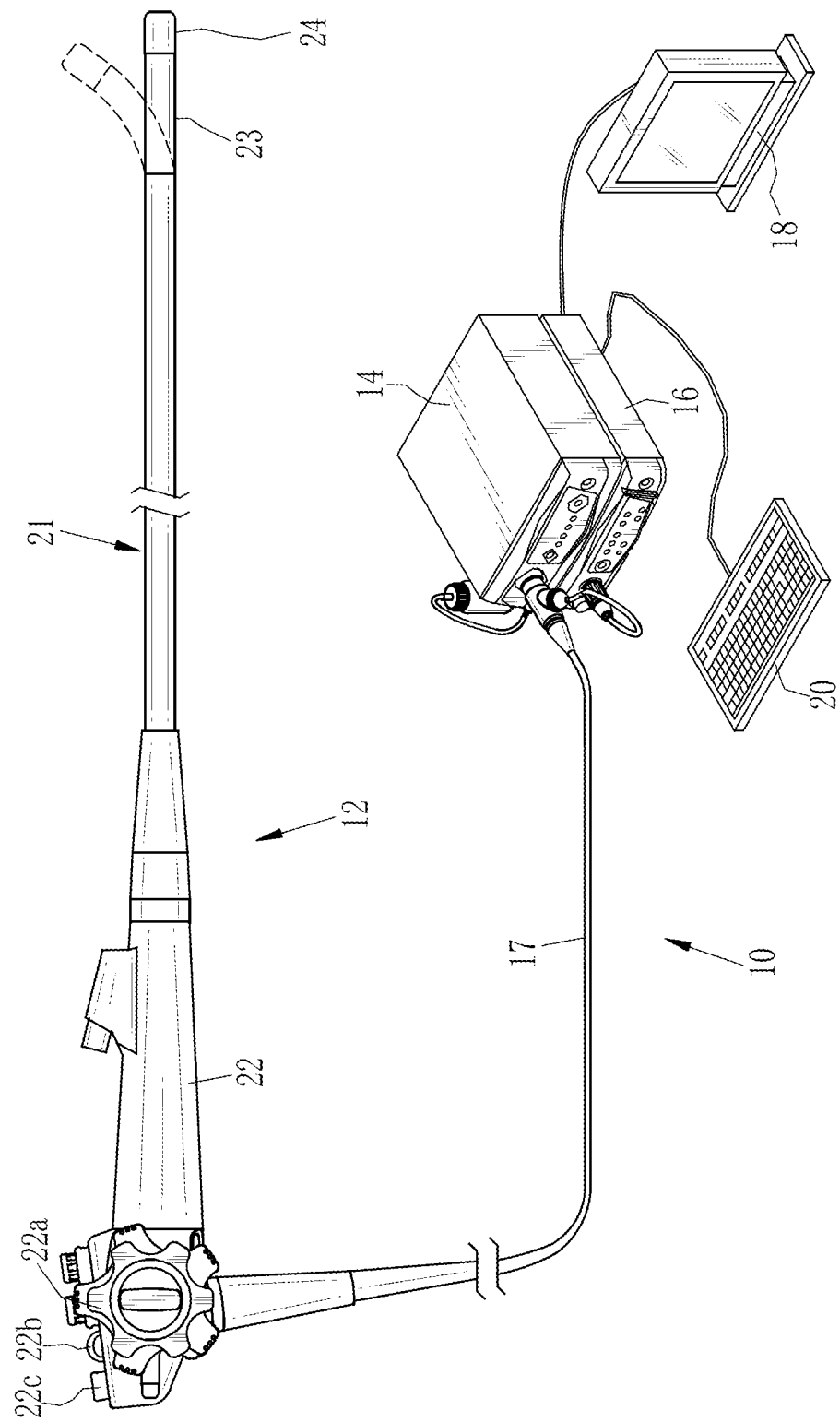
FIG. 1 is an external view of an endoscope system.

As illustrated in FIG. 1, an endoscope system 10 comprises an endoscope 12, a light source device 14, a processor device 16, a monitor 18 and a console 20. The endoscope 12 is connected to the light source device 14 optically and to the processor device 16 electrically. The endoscope 12 includes an insertion section 21 for being inserted in a patient, a control handle 22 provided on a proximate end of the insertion section 21, and a flexible portion 23 and a distal portion 24 provided on the distal portion side of the insertion section 21. The flexible portion 23 can be bent through an operation of an angle knob 22a of the control handle 22. Through this bending action, the distal portion 24 can be turned to a desired direction. In addition, in the control handle 22, a zoom control unit 22b and a freeze button 22c to store a static image are provided other than the angle knob 22a.

The light source device 14 is a device for generating illumination light to irradiate an observation object, and is connected to the endoscope 12 optically through a universal cord 17. The illumination light generated by the light source device 14 is guided by the universal cord 17 and a light guide 41 (see FIG. 2) provided inside the endoscope 12, and irradiates the observation object from the distal portion 24. In addition, the light source device 14 has plural semiconductor light sources as a light source to generate the illumination light, and is able to control an intensity distribution (so-called an optical spectrum) of each wave length component of the illumination light by controlling turning on/off or emission amount of each of the semiconductor light sources. The light source device 14 is connected to the processor device 16 electrically, and controls an amount and an optical spectrum of the illumination light based on a control signal from the processor device 16.

The processor device 16 is connected to the endoscope 12 electrically through the universal cord 17, obtains image signals from an image sensor 48 (see FIG. 2) provided in the distal portion 24, generates an image of the observation object (hereinafter referred to as the observation image), and outputs the image to the monitor 18. The monitor 18 displays the observation image and information relating to the observation image (hereinafter referred to as "the observation image and so on"). The console 20 functions as an UI (user interface) for accepting input operations of function settings and so on. In addition, to the processor device 16, a storage unit (not illustrated) for memorizing the observation image and so on are connected.

Figure 2:
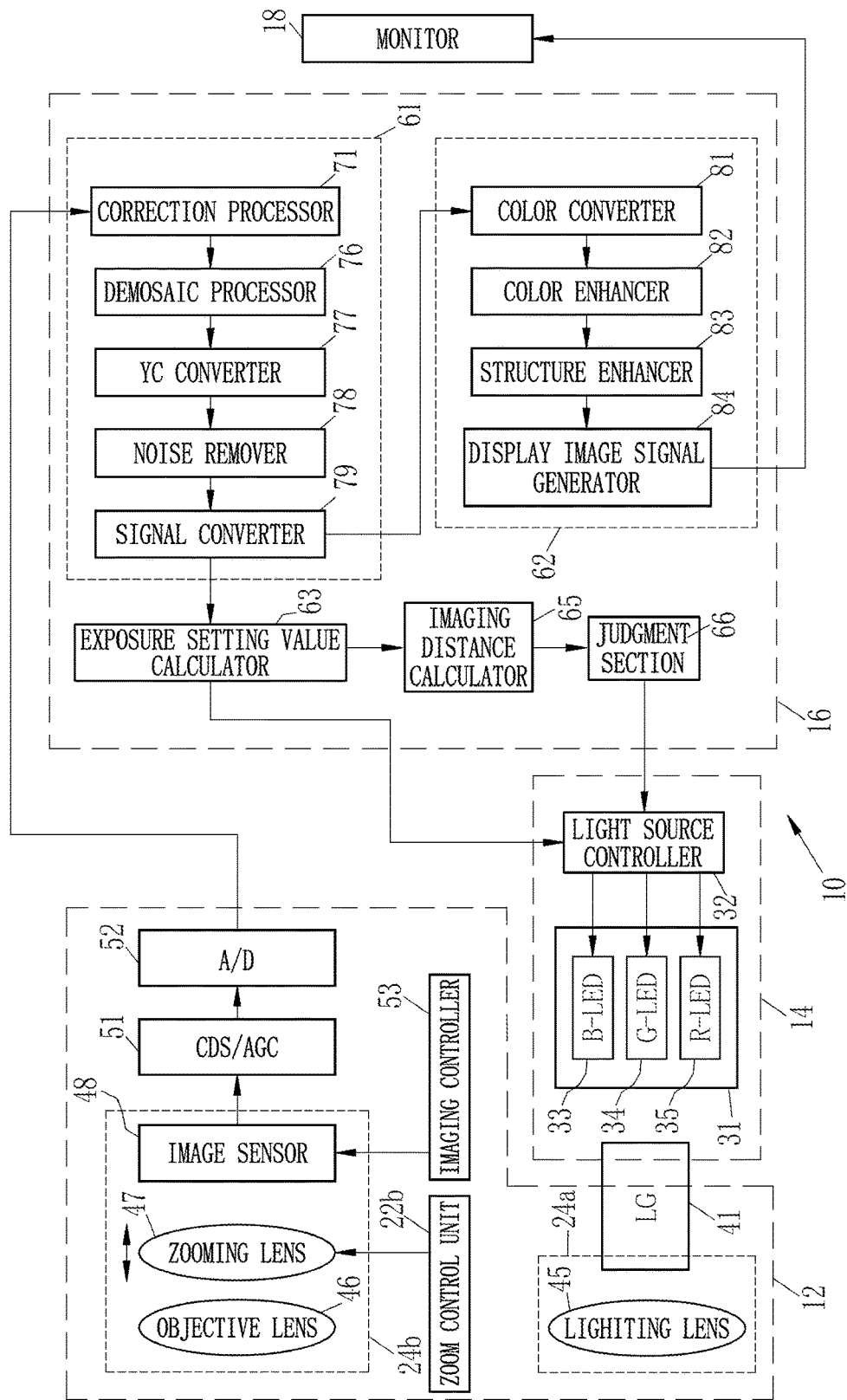
FIG. 2 is a block diagram of the endoscope system.
Figure 3:
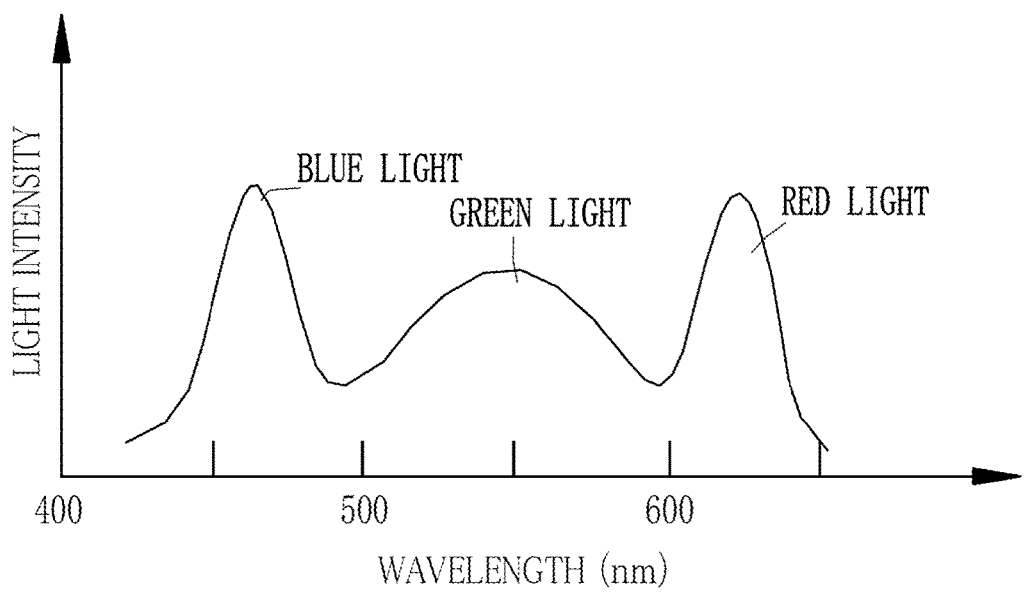
FIG. 3 is a graph illustrating an optical spectrum of illumination light (reference white light)

As illustrated in FIG. 2, the light source device 14 includes an LED (Light Emitting Diode) light source unit 31 and a light source controller 32. The LED light source unit 31 has a B-LED 33, a G-LED 34 and an R-LED 35 as the semiconductor light source to generate the illumination light. As illustrated in FIG. 3, the B-LED 33 emits light in a blue wavelength band having the central wavelength of 445-460 nm (hereinafter simply referred to as the blue light), and the G-LED 34 emits light in a green wavelength band of approximately 500-600 nm described in a normal distribution (hereinafter simply referred to as the green light) In addition, the R-LED 35 emits light in a red wavelength band of 600-650 nm (hereinafter simply referred to as the red light). The central wavelength of the red light is approximately 620-630 nm. The illumination light that the light source device 14 generates has an optical spectrum made by putting each light from the LEDs 33, 34 and 35 together. In case the LED 33, 34 and 35 emit light in a predetermined ratio of emission amount, the illumination light becomes white light having an optical spectrum illustrated in FIG. 3. The white light having the optical spectrum illustrated in FIG. 3 is hereinafter referred to as the reference white light. The reference white light is the white light having the most suitable optical spectrum to image the observation object in natural colors, among illumination light having various optical spectrums that can be produced with using the LEDs 33, 34 and 35. The optical spectrum of the reference white light is predetermined by an experiment or another method.

The light source controller 32 controls turning on/off or emission amount of each LED 33, 34 and 35 of the LED light source unit 31. The emission amount and the optical spectrum of the illumination light are controlled through the LEDs 33, 34 and 35 under control of the light source controller 32. Specifically, the light source controller 32 automatically controls emission amount of the illumination light to be suitable for imaging the observation object, by controlling emission amount of each LED 33, 34, and 35 with keeping the ratio of emission amount of each LED 33, 34, and 35 based on an exposure setting value which is calculated in an exposure setting value calculator 63.

Figure 4:
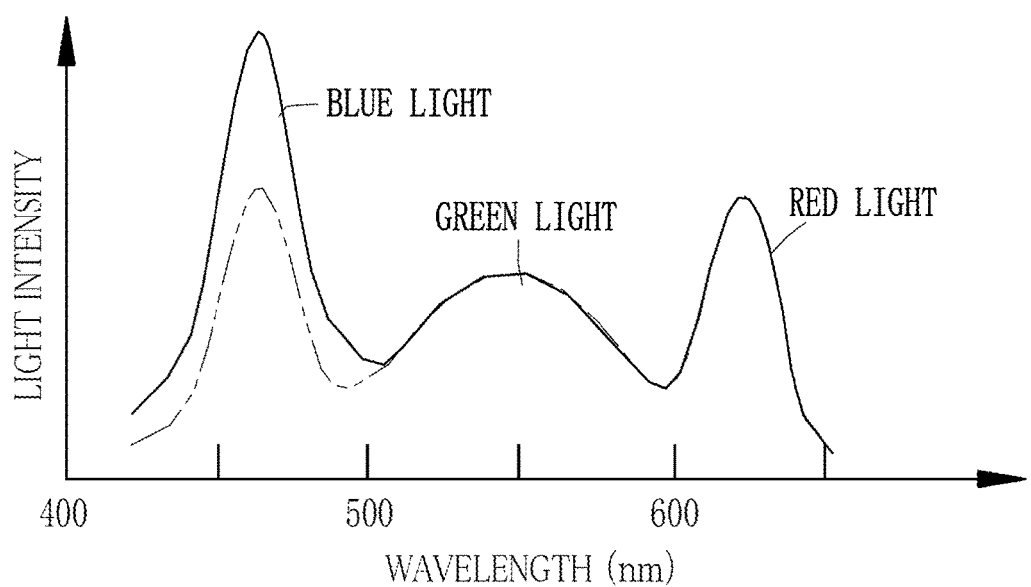
FIG. 4 is a graph illustrating an optical spectrum of illumination light in which a component of blue light is increased.
Figure 5:
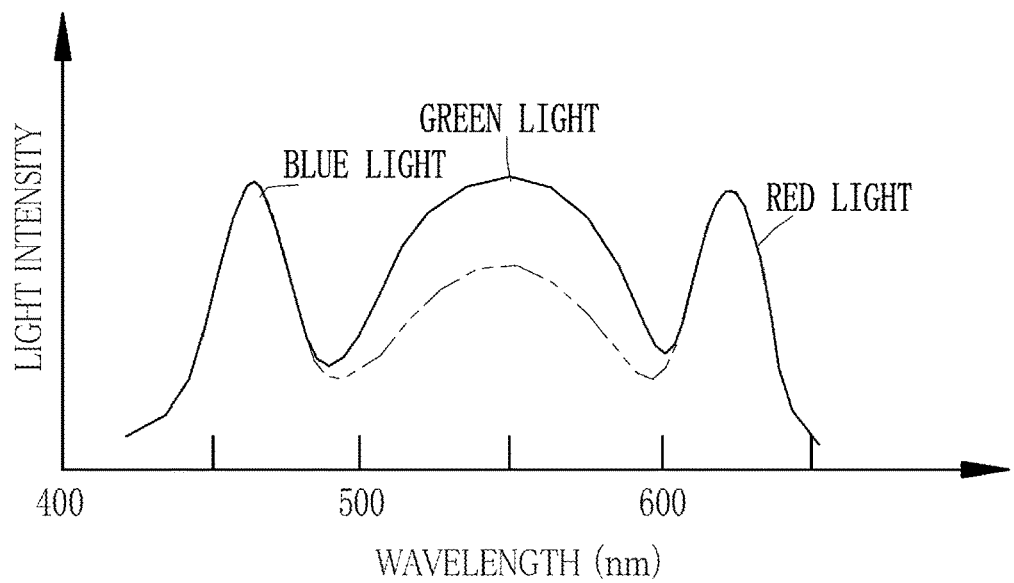
FIG. 5 is a graph illustrating an optical spectrum of illumination light in which a component of green light is increased.

In addition, the light source controller 32 controls the optical spectrum of the illumination light by controlling a balance of emission amount of each LED 33, 34 and 35 based on an imaging distance which is calculated in an imaging distance calculator 65. More specifically, the light source controller 32 controls the optical spectrum according to the imaging distance, by receiving a judgment result of a comparison between the imaging distance and a predetermined threshold value from a judgment section 66 and controlling the optical spectrum based on the judgment result. For example, in case the judgment result input by the judgment section 66 represents that the imaging distance is no more than the threshold value (the imaging distance is short), at least an amount of the blue light is increased from the reference white light illustrated with an alternate long and two short dashes line, as illustrated in FIG. 4. That is, the light source controller 32 increases the component of the blue light included in the illumination light as the imaging distance becomes shorter. Accordingly, incase the imaging distance is short, white light with a lot of blue light component is irradiated on the observation object as the illumination light. On the other hand, in case the judgment result input by the judgment section 66 represents that the imaging distance is more than the threshold value (the imaging distance is long), at least an amount of the green light is increased from the reference white light illustrated with an alternate long and two short dashes line, as illustrated in FIG. 5. That is, the light source controller 32 increases the component of the green light included in the illumination light as the imaging distance becomes shorter. Accordingly, in case the imaging distance is long, white light with a lot of green light component is irradiated on the observation object as the illumination light.

The blue light, green light, and red light from the LED light source unit 31 are incident on the light guide (LG) 41 through optical materials such as a condenser lens, an optical fiber, and a multiplexer (none is illustrated). The light guide 41 is embedded in the universal cord 17 (see FIG. 1) and the endoscope 12. A distal portion of the light guide 41, from which illumination light is irradiated, is located in the distal portion 24.

The distal portion 24 of the endoscope 12 has an illumination optical system 24a and an imaging optical system 24b. A lighting lens 45 is provided in the illumination optical system 24a, and illumination light is irradiated toward observation object through the lighting lens 45 from the light guide 41.

The imaging optical system 24b includes an objective lens 46, a zooming lens 47, and the image sensor 48. Reflected light of the illumination light from the observation object is incident on the image sensor 48 through the objective lens 46 and the zooming lens 47. An image of the observation object is in this way imaged on the image sensor 48. The zooming lens 47 is a lens for enlarging or reducing an image of the observation object imaged on the image sensor 48, and moves along an optical axis through an operation of the zoom control unit 22b. Accordingly, an imaging magnification of the imaging optical system 24b is variable.

Figure 6:
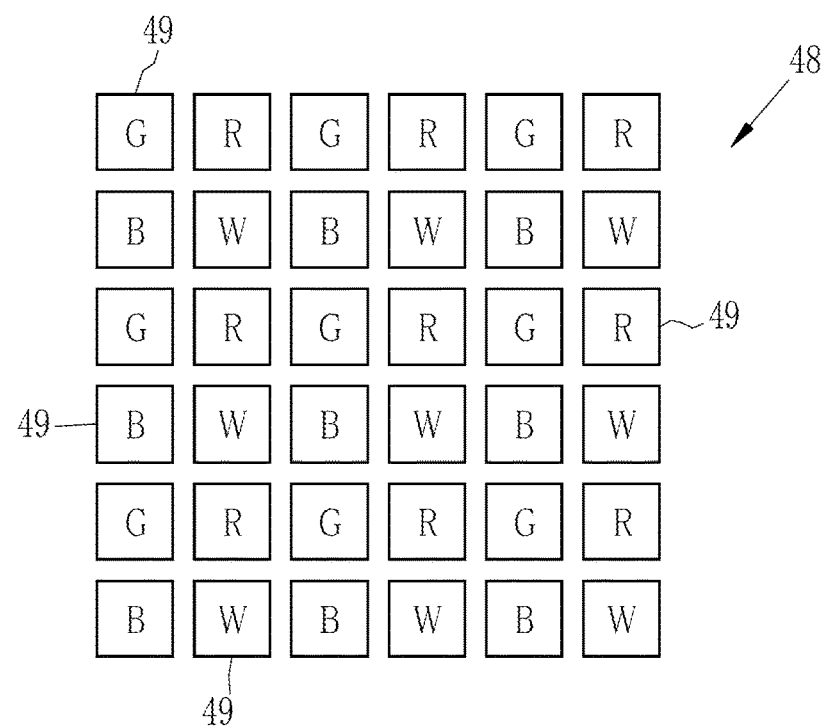
FIG. 6 is an explanatory view illustrating an pixel arrangement of an image sensor.
Figure 7:
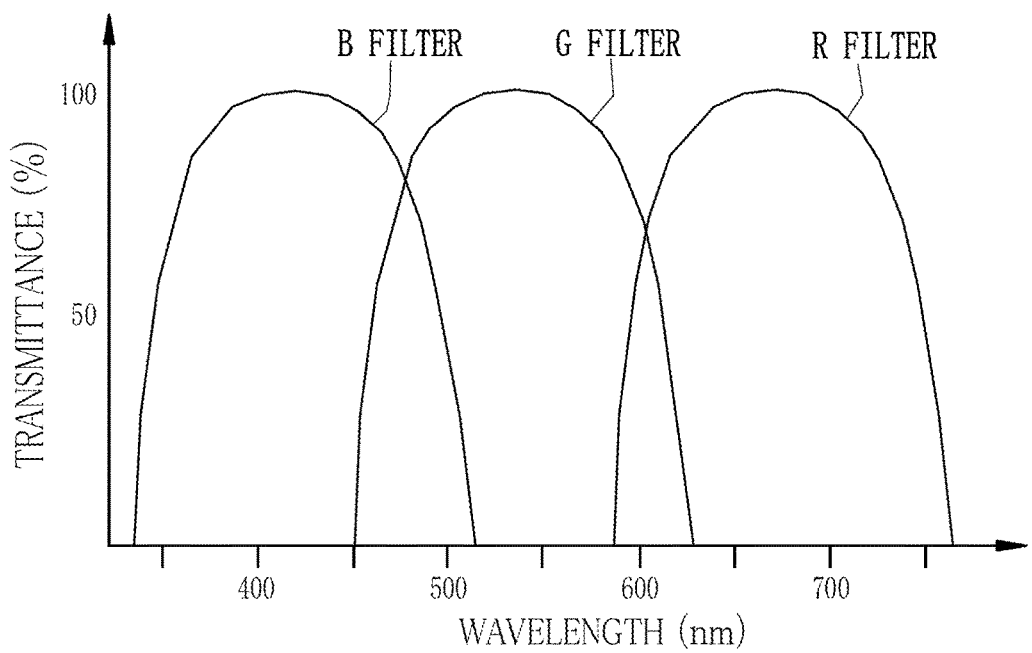
FIG. 7 is a graph illustrating spectral transmittance of a color filter.

The image sensor 48 images the observation object with the reflected light of the illumination light, and outputs image signals. As the image sensor 48, for example a CCD (Charge Coupled Device) image sensor and a CMOS (Complementary Metal-Oxide Semiconductor) image sensor can be used. As illustrated in FIG. 6, the image sensor 48 is a color image sensor having plural pixels 49 squarely arranged on an imaging surface. In each of the pixels 49, a color filter of one of a B filter, a G filter, an R filter, a W filter is provided. As illustrated in FIG. 7, the B filter has a spectral transmittance of 380-560 nm, the G filter has a spectral transmittance of 450-630 nm, and the R filter has a spectral transmittance of 580-760 nm. In this embodiment, the W filter has a spectral transmittance of at least 380-760 nm. Accordingly, a B pixel (blue pixel) where the B filter is provided receives blue light among light of each color wavelength band included in the reflected light of the illumination light from the observation object, and outputs a B image signal. In the same way, a G pixel (green pixel) where the G filter is provided receives green light and outputs a G image signal, and an R pixel (red pixel) where the R filter is provided receives red light and outputs an R image signal. A W pixel (specific pixel) where the W filter is provided receives blue light, green light and red light and outputs a W image signal.

In addition, as an arrangement of the B pixels, the G pixels, the R pixels and the W pixels, since a row where the G pixel and the R pixel are placed in turn and a row where the B pixel and the W pixel are placed in turn are alternately placed, the G pixel and the B pixel are adjacent up and down, and the R pixel and the W pixel are adjacent up and down (see FIG. 6). Therefore, the pixel arrangement of the image sensor 48 becomes a Bayer array in case the W pixel is replaced with the G pixel.

The image signal of each color output from the image sensor 48 is transmitted to a CDS (correlated double sampling)/AGC (automatic gain control) circuit 51 (see FIG. 2). The CDS/AGC circuit 51 applies a correlated double sampling (CDS) and an automatic gain control (AGC) to the analog image signal output from the image sensor 48. Accordingly, the CDS/AGC circuit 51 functions as a gain controller that controls a gain when the image sensor 48 outputs the image signals. The image signals output from the CDS/AGC circuit 51 is converted into digital image signals by an A/D converter 52. The digitized image signals are input into the processor device 16. An imaging controller 53 performs imaging control of the image sensor 48 based on control signals input from the processor device 16.

The processor device 16 includes an image signal acquisition unit 61, an image-processing unit 62, an exposure setting value calculator 63, the imaging distance calculator 65, and the judgment section 66.

The image signal acquisition unit 61 acquires the image signal of each color from the image sensor 48. The image signal acquisition unit 61 includes a correction processor 71, a demosaic processor 76, an YC converter 77, a noise remover 78, and a signal converter 79. Among these components, the correction processor 71, the demosaic processor 76 and the YC converter 77 are realized by a so-called DSP (Digital Signal Processing unit).

The correction processor 71 includes a defect correction processor, an offset processor, a gain correction processor, a linear matrix processor, and a gamma conversion processor. The defect correction processor receives the image signals of each color and applies a defect correction process for correcting a signal value of a pixel corresponding to a defect pixel in the image sensor 48. The offset processor removes a dark current component from the image signal after the defect correction process, and sets an accurate zero level. The gain correction processor corrects the signal level of each of the image signals by multiplying the image signal of each color after the offset process by a specific gain. The linear matrix processor applies a linear matrix process for improving color reproductivity to the image signal of each color after the gain correction process. The gamma conversion processor applies a gamma conversion process for adjusting image brightness and image saturation to the image signal after the linear matrix process.

The demosaic processor 76 applies a demosaic process (it is also called an isotropy process or a synchronization process) to the image signal after the gamma conversion process, so that a signal of a lacked color of each pixel is generated by interpolation. All pixels come to have signals of RGB by this demosaic process. In addition, the demosaic process is different according to an imaging distance which the imaging distance calculator 65 calculates. For example, in case the imaging distance is long, a first demosaic process is applied to the image signal obtained under illumination light where green light is increased from the reference white light. On the other hand, in case the imaging distance is short, a second demosaic process is applied to the image signal obtained under illumination light where blue light is increased from the reference white light.

Figure 8:
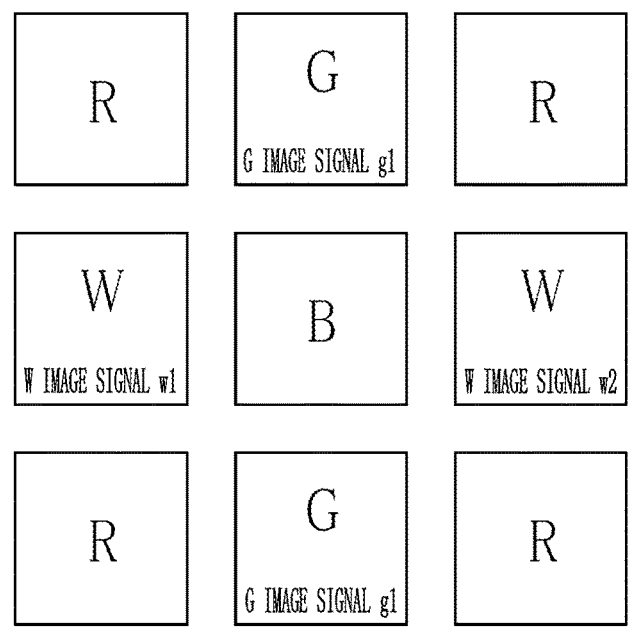
FIG. 8 is an explanatory view illustrating a way to obtaining a G image signal of a B pixel position by a first demosaic process.
Figure 9:
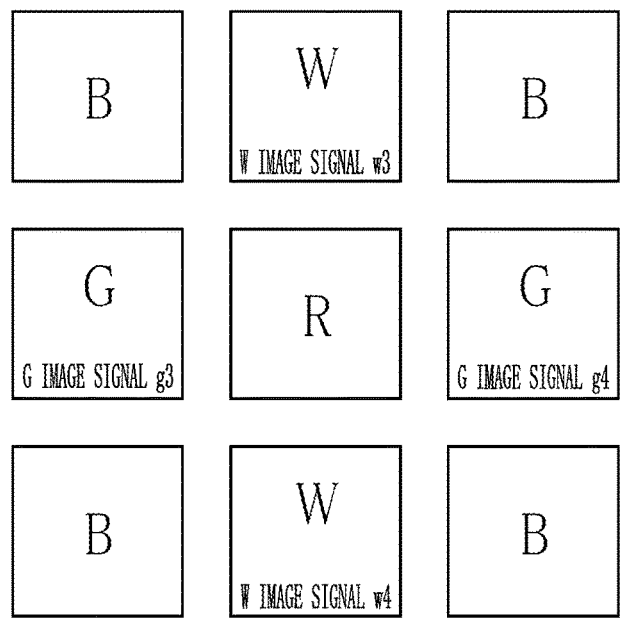
FIG. 9 is an explanatory view illustrating a way to obtaining a G image signal of an R pixel position by the first demosaic process.

The first demosaic process is the demosaic process in which the W pixel is used as the G pixel. In the first demosaic process, as illustrated in FIG. 8, the average value of the G image signals (the signal values of the G pixels) g1, g2 of the G pixel positions adjacent up and down of the B pixel and the W image signals (the signal values of the W pixels) w1, w2 of the W pixel positions adjacent right and left of the B pixel is calculated. The average value is used as the G image signal of the B pixel position on the image sensor 48. Accordingly, in the first demosaic process, the G image signal of the B pixel position becomes "(g1+g2+w1+w2)/4". In the same way, in the first demosaic process, as illustrated in FIG. 9, the average value of the G image signals (the signal values of the G pixels) g3, g4 of the G pixel positions adjacent right and left of the R pixel and the W image signals (the signal values of the W pixels) w3, w4 of the W pixel positions adjacent up and down of the R pixel is calculated. The average value is used as the G image signal of the R pixel position on the image sensor 48. Accordingly, in the first demosaic process, the G image signal of the R pixel position becomes "(g3+g4+w3+w4)/4".

Figure 10:
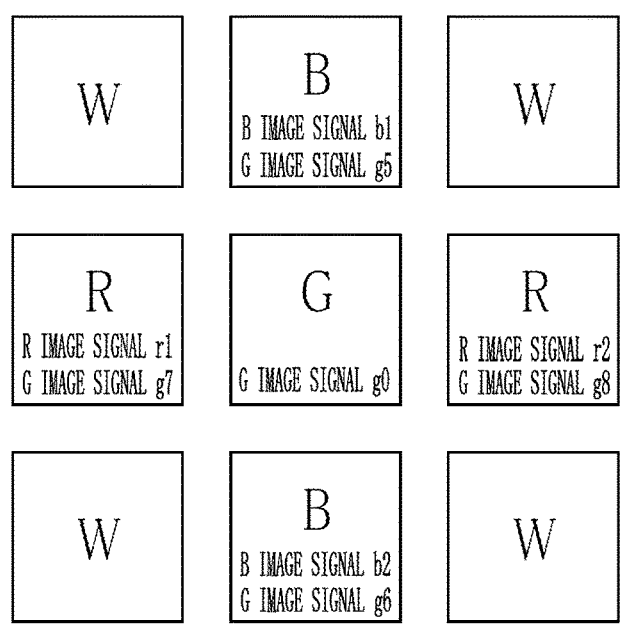
FIG. 10 is an explanatory view illustrating a way to obtaining B and R image signals of a G pixel position by the first demosaic process.

In addition, in the first demosaic process, as illustrated in FIG. 10, the B image signal of the G pixel position is calculated with use of the G image signal (the signal value of the G pixel) g0 of the G pixel position, the B image signals (the signal values of the B pixels) b1, b2 of the B pixel positions adjacent up and down of the G pixel, and the G image signals g5, g6 of the B pixel position calculated as described above. Specifically, the B image signal of the G pixel position becomes "g0+(b1−g5+b2−g6)/2", In the same way, the B image signal of the G pixel position is calculated with use of the G image signal g0 of the G pixel position, the R image signals (the signal values of the R pixels) r1, r2 of the R pixel positions adjacent right and left of the G pixel, and the G image signals g7, g8 of the R pixel position calculated as described above. Specifically, the R image signal of the G pixel position becomes "g0+(r1−g7+r2−g8)/2".

Figure 11:
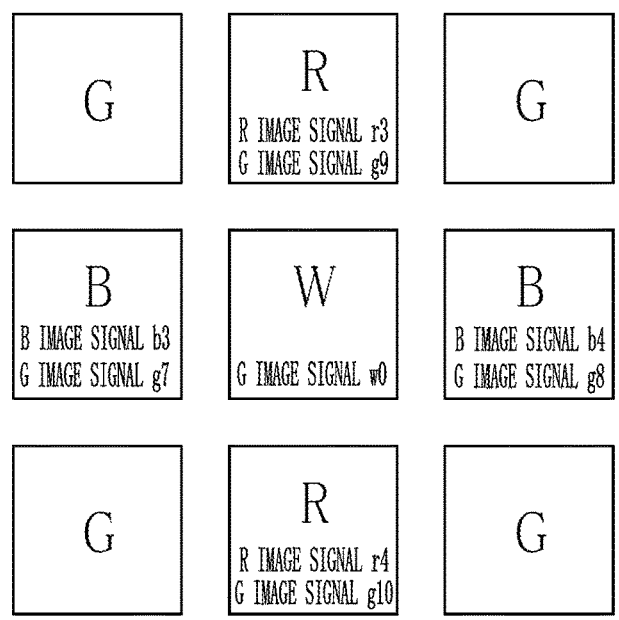
FIG. 11 is an explanatory view illustrating a way to obtaining B and R image signals of a W pixel position by the first demosaic process.

Further, in the first demosaic process, as illustrated in FIG. 11, since the W pixel is used as the G pixel, the signal value w0 of the W pixel is used as the G image signal of the W pixel position. The way to calculate the B image signal and the R image signal of the W pixel position is the same as the way to calculate each signal value of the B image signal and the R image signal of the G pixel position (see FIG. 10). Accordingly, the B image signal of the W pixel position becomes "w0+(b3−g7+b4−g8)/2", calculated with use of the G image signal w0 of the W pixel position, the B image signals (the signal values of the B pixels) b3, b4 of the B pixel positions adjacent right and left of the W pixel, and the G image signals g7, g8 of the B pixel position calculated as described above. In addition, the R image signal of the W pixel position becomes "w0+(r3−g9+r4−g10)/2", calculated with use of the G image signal w0 of the W pixel position, the R image signals (the signal values of the R pixels) r3, r4 of the R pixel positions adjacent up and down of the W pixel, and the G image signals g9, g10 of the R pixel position calculated as described above.

Figure 12:
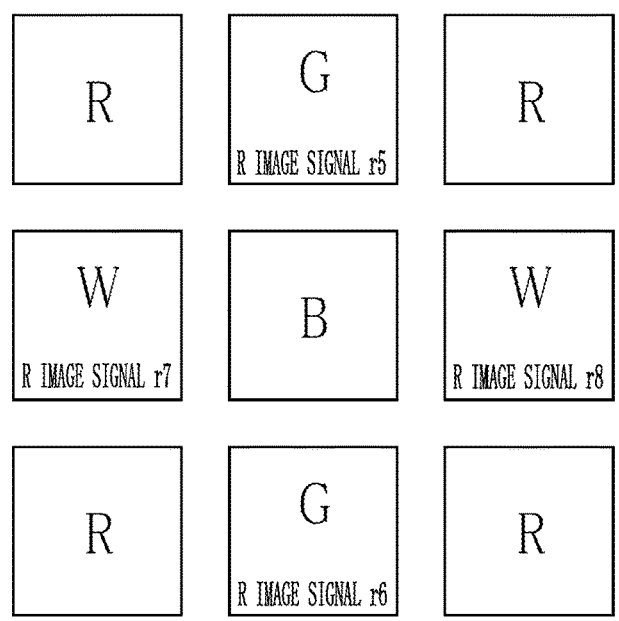
FIG. 12 is an explanatory view illustrating a way to obtaining an R image signal of a B pixel position by the first demosaic process.
Figure 13:
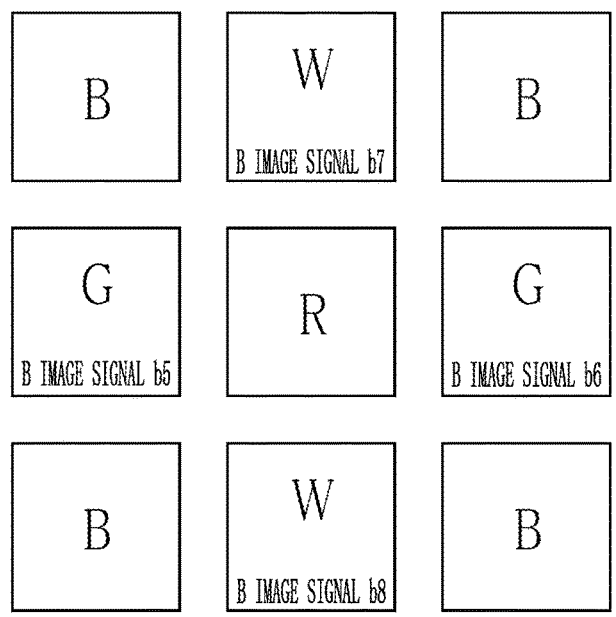
FIG. 13 is an explanatory view illustrating a way to obtaining a B image signal of an R pixel position by the first demosaic process.

The R image signal of the B pixel position is calculated with use of the R image signal of the G pixel position calculated as described above, and the R image signal of the W pixel position. Specifically, in the first demosaic process, as illustrated in FIG. 12, the average value "(r5+r6+r7+r8)/4" of the R image signals r5, r6 of the G pixel positions adjacent up and down of the B pixel and the R image signals r7, r8 of the W pixel positions adjacent right and left of the B pixel is used as the R image signal of the B pixel position. In the same way, the B image signal of the R pixel position is calculated with use of the B image signal of the G pixel position calculated as described above, and the R image signal of the W pixel position. Specifically, in the first demosaic process, as illustrated in FIG. 13, the average value "(b5+b6+b7+b8)/4" of the B image signals b5, b6 of the G pixel positions adjacent right and left of the R pixel and the B image signals b7, b8 of the W pixel positions adjacent up and down of the R pixel is used as the B image signal of the R pixel position.

Figure 14:
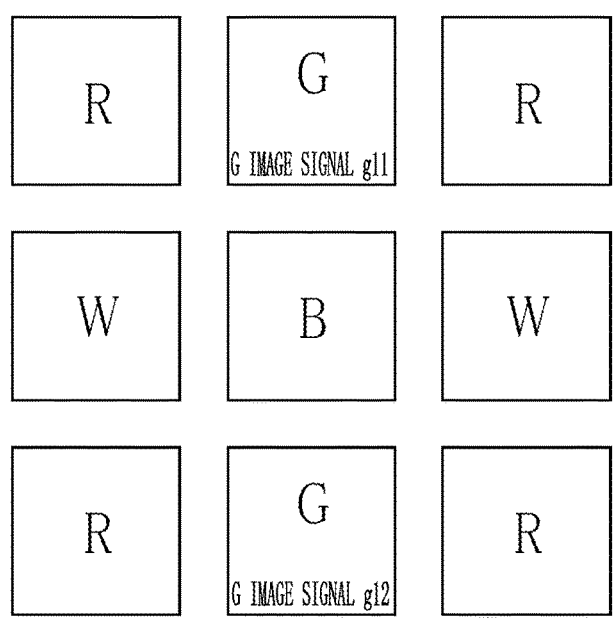
FIG. 14 is an explanatory view illustrating a way to obtaining a G image signal of a B pixel position by a second demosaic process.
Figure 15:
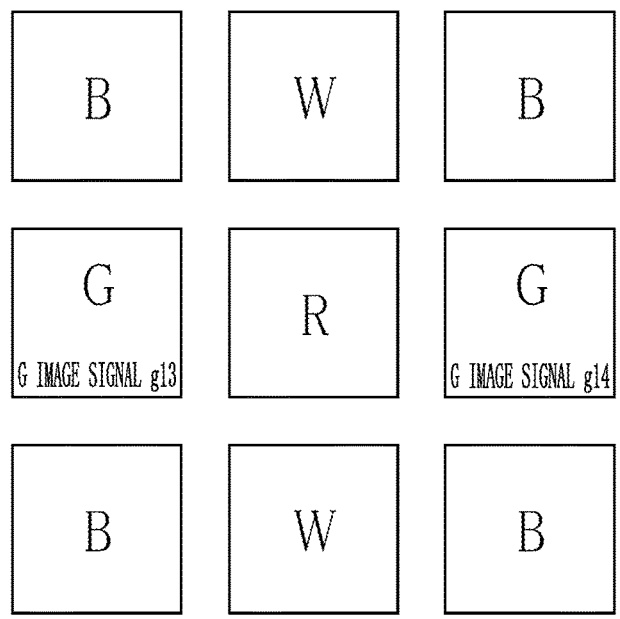
FIG. 15 is an explanatory view illustrating a way to obtaining a G image signal of an R pixel position by the second demosaic process.

The second demosaic process is the demosaic process in which the W pixel is used as the B pixel. As illustrated in FIG. 14, in the second demosaic process, the G image signal of the B pixel position is calculated based on the G image signals (the signal values of the G pixels) of the G pixel positions adjacent up and down of the B pixel. Specifically, the average value "(g11+g12)/2" of the G image signals g11, g12 of the G pixel positions adjacent up and down of the B pixel is used as the G image signal of the B pixel position. In the same way, the G image signal of the R pixel position is calculated based on the G image signals (the signal values of the G pixels) of the G pixel positions adjacent right and left of the R pixel. Specifically, as illustrated in FIG. 15, the average value "(g13+g14)/2" of the G image signals g13, g14 of the G pixel positions adjacent right and left of the R pixel is used as the G image signal of the R pixel position.

Figure 16:
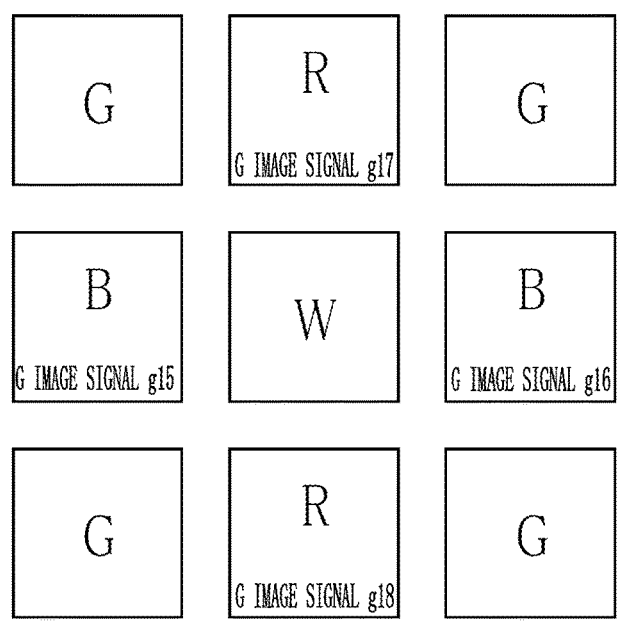
FIG. 16 is an explanatory view illustrating a way to obtaining a G image signal of a W pixel position by the second demosaic process.

Further, in the second demosaic process, the G image signal of the W pixel position that is used as the B pixel is calculated with use of the G image signal of the B pixel position calculated as described above, and the G image signal of the R pixel position. Specifically, as illustrated in FIG. 16, the average value "(g15+g16+g17+g18)/4" of the G image signals g15, g16 of the B pixel positions adjacent right and left of the W pixel and the G image signals g17, g18 of the R pixel positions adjacent up and down of the W pixel is used as the G image signal of the W pixel position.

The method for calculation of the B image signal and the R image signal of the G pixel position in the second demosaic process is the same as the first demosaic process (see FIG. 10). In the second demosaic process, since the W pixel is used as the B pixel, the signal value of the W pixel is used as the B image signal of the W pixel position. The R image signal of the W pixel position is calculated by the same way as calculating the R image signal of the B pixel position in the first demosaic process, with use of the G image signal of the W pixel position calculated as described above, and the G image signal and the R image signal of the R pixels adjacent up and down of the W pixel (see FIG. 11). Note that the method for calculation of the R image signal of the B pixel position and the method for calculation of the B image signal of the R pixel position in the second demosaic process are the same as the first demosaic process (see FIGS. 12 and 13).

As described above, although the first and second demosaic processes are different from each other in the processing method, both of the demosaic processes make all pixels have signals of the RGB.

The YC converter 77 applies an YC conversion process to the image signal after the demosaic process, so that a luminance signal Y and color difference signals Cb, Cr are generated. The luminance signal Y and color difference signals Cb, Cr that the YC converter 77 produced are input into the noise remover 78.

The noise remover 78 applies a noise removal process for example of a moving average method or a median filter method to the input signal. The signals where noise is removed are input into the signal converter 79, converted into image signals of the RGB again, and then input into the image-processing unit 62 and the exposure setting value calculator 63.

The image-processing unit 62 has a color converter 81, a color enhancer 82, a structure enhancer 83 and a display image signal generator 84. The color converter 81 generates RGB image data in which the input BGR color image signals are respectively assigned to the RGB pixels. The color converter 81 further applies a color conversion process such as a 3×3-matrix process, a gradation conversion process, and a three-dimensional LUT process to the RGB image data.

The color enhancer 82 applies various color enhancement processes to the RGB image data after the color conversion process. The structure enhancer 83 applies a structure enhancement process such as a spatial frequency emphasis to the RGB image data after the color enhancement process. The RGB image data after the structure enhancement process applied by the structure enhancer 83 is input into the display image signal generator 84 as the observation image. The display image signal generator 84 converts the observation image into signals for display format (display image signals, e.g., a luminance signal Y and color difference signals Cb, Cr), and input the display image signals to the monitor 18. In this way, the observation image is displayed on the monitor 18.

The exposure setting value calculator 63 calculates the exposure setting value based on the image signal input from the signal converter 79. The exposure setting value is a control parameter for specifying an exposure amount to image the observation object. In this embodiment, since the exposure amount is controlled by an amount of the illumination light, the exposure setting value is the control parameter to specify the amount of the illumination light. The exposure setting value calculator 63 calculates for example an average value of the brightness of the each pixel (hereinafter referred to as the average brightness) with use of the input image signals, for calculation of the exposure setting value. In case the average brightness is higher than a brightness determined for example by setting (hereinafter referred to as the set brightness), the exposure setting value that decreases the exposure amount is calculated so that the average brightness becomes close to the set brightness. On the contrary, in case average brightness is lower than the set brightness, the exposure setting value that increases the exposure amount is calculated so that the average brightness becomes close to the set brightness. In case the average brightness is approximately equal with the set brightness, the exposure setting value for keeping the average brightness is calculated. The exposure setting value calculated in this way is input into the light source controller 32 to be used for determination of an amount of the illumination light. In addition, the exposure setting value is input into the imaging distance calculator 65 to be used for calculation of the imaging distance.

The imaging distance calculator 65 calculates the imaging distance based on the exposure setting value input from the exposure setting value calculator 63. The exposure setting value is related to the imaging distance, though is the control parameter to specify the amount of illumination light as described above. For example, incase the imaging distance becomes shorter, the exposure setting value becomes smaller, since the reflection amount of the illumination light from the observation object becomes larger. On the contrary, in case the imaging distance becomes longer, the exposure setting value becomes larger, since the reflection amount of the illumination light from the observation object becomes smaller. The imaging distance calculator 65 has a table (not illustrated) which correlates this exposure setting value with the imaging distance, and calculates the imaging distance from the exposure setting value with referring to this table. The table that correlates the exposure setting value with the imaging distance is previously obtained for example by an experiment. The imaging distance calculated by the imaging distance calculator 65 is input into the judgment section 66, to be used for determining whether the imaging distance is long or short.

The judgment section 66 compares the imaging distance calculated by the imaging distance calculator 65 with a predetermined threshold value. In case the imaging distance is less than the threshold value, the judgment section 66 judges that the imaging distance is short, and the judgment result is input into the light source controller 32. On the other hand, in case the imaging distance is more than the threshold value, the judgment section 66 judges that the imaging distance is long, and the judgment result is input into the light source controller 32. The light source controller 32 decides the optical spectrum of the illumination light based on the judgment result input from the judgment section 66 (i.e., according to the length of the imaging distance). Note that the judgment section 66 may be provided in the light source device 14, and the light source controller 32 may perform the judgment of the imaging distance.

Figure 17:
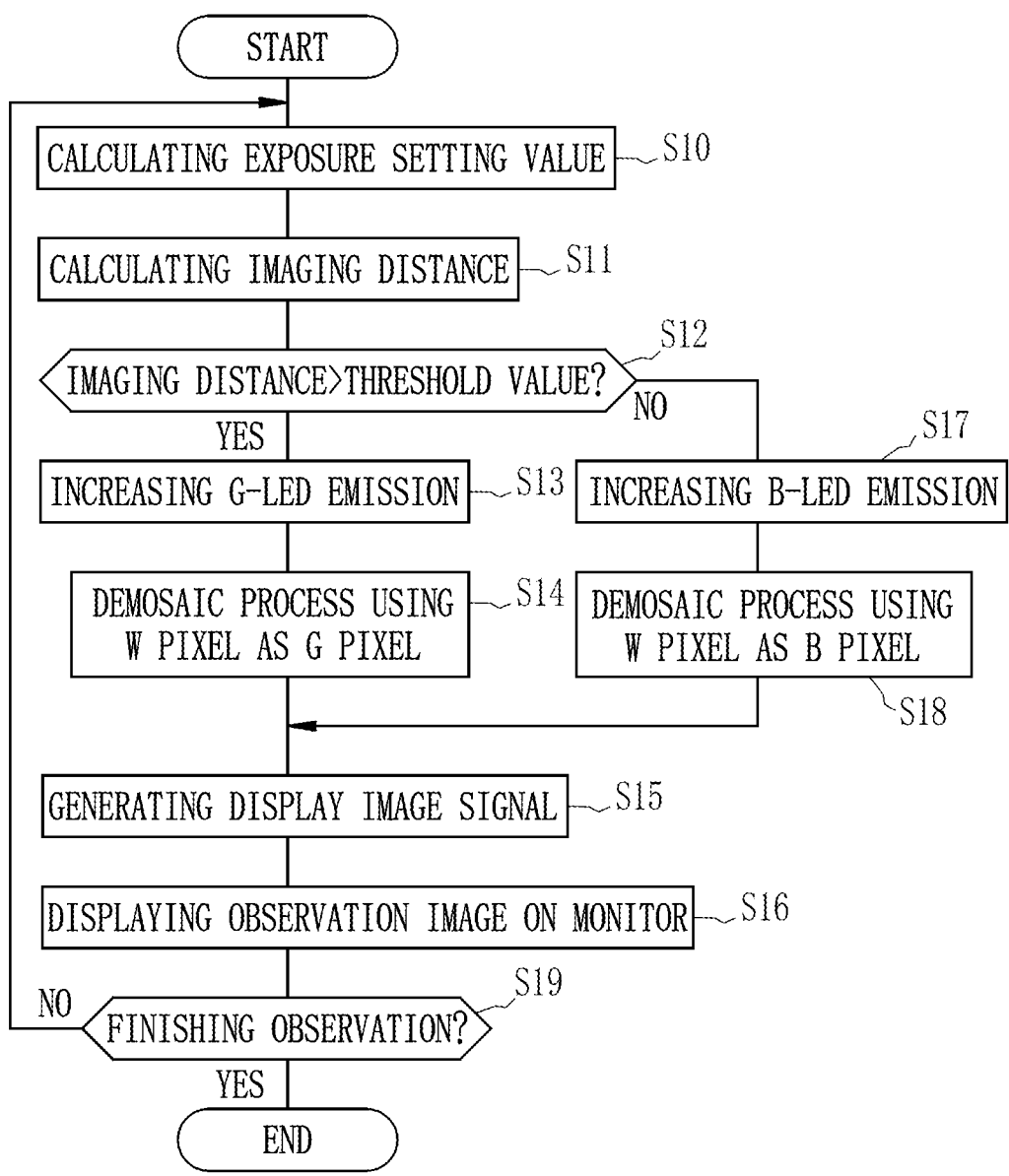
FIG. 17 is a flow chart illustrating an operation of the endoscope system.
Figure 18:
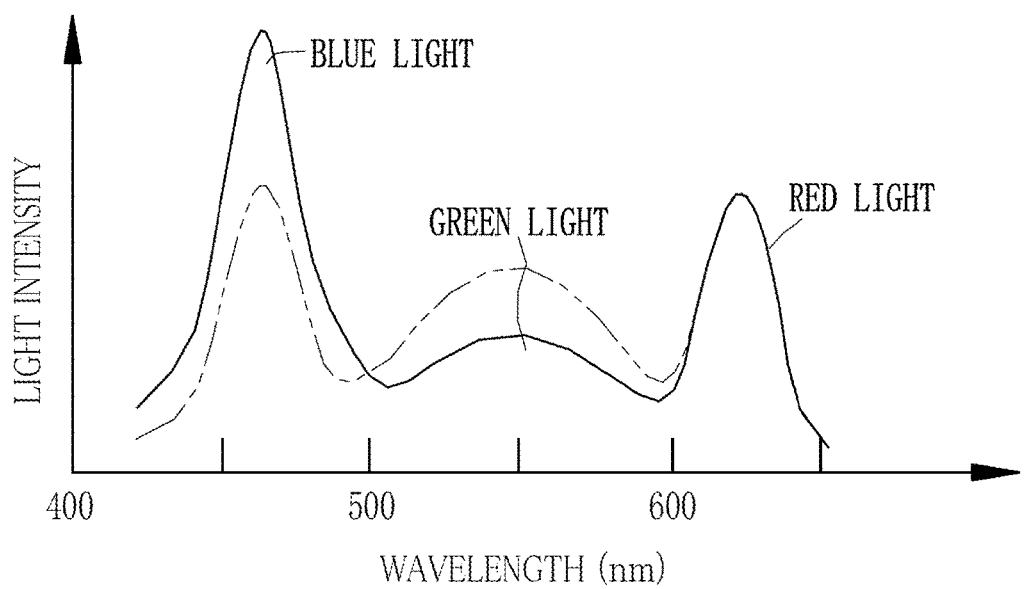
FIG. 18 is a graph illustrating an optical spectrum of illumination light in which a component of blue light is increased and a component of green light is decreased from the reference white light.

Next, an operation of the endoscope system 10 of this embodiment will be explained with referring to a flowchart of FIG. 17. When an observation is started using the endoscope system 10, the light source device 14 produces, for example, the reference white light as the illumination light. The image sensor 48 images the observation object under the reference white light and outputs image signals. After the image sensor 48 outputs the image signals, the exposure setting value calculator 63 calculates the exposure setting value (S10: exposure setting value calculation step). Furthermore, the imaging distance calculator 65 calculates the imaging distance based on the exposure setting value (S11: imaging distance calculation step).

After the exposure setting value and the imaging distance are calculated, the light source controller 32 controls light quantity and an optical spectrum of the illumination light based on these. Specifically, in case the imaging distance is longer than the threshold value (S12: YES), the light source controller 32 increases light emission of the G-LED 34 from the balanced light emission (the ratio of light quantity) of the B-LED 33, G-LED 34 and R-LED 35 of the reference white light used as the illumination light, and controls quantity of the illumination light to the quantity based on the exposure setting value (S13: light source controlling step). In this way, a white light having the optical spectrum with green light component increased from the reference white light is irradiated on the observation object as the illumination light.

In this way, incase the observation object is imaged under the illumination light with increased green light component, a signal value of the W pixel of the image sensor 48 becomes close to a signal value of the G pixel rather than that of a so-called white pixel, because the received amount of green light becomes larger than the case of imaging the observation object under the reference white light. In case the green light component is predominantly larger than the red light component and the blue light component included in the illumination light, the signal value of the W pixel is about the same with the signal value of the G pixel. Therefore, the demosaic processor 76 generates a signal of a deficient color of the each pixel by the first demosaic process which considers the W pixel to be the G pixel (S14). Then the display image signals are generated (S15) based on the image signals to which the first demosaic process was applied, and the observation image is displayed on the monitor 18 (S16).

As described above, in case the imaging distance is long, by increasing the green light component of the illumination light and applying the first demosaic process which considers the W pixel to be the G pixel to generate and display the observation image, the same effect as in case the W pixel of the image sensor 48 is the G pixel from the beginning is obtained. In other words, it is similar to imaging the observation object with an image sensor where the number of G pixels is twice those of the B pixels and the R pixels, so the green resolution to which human eyes are the most sensitive improves. In addition, since the G pixel mostly contributing to the brightness of the observation image (brightness at the time of displaying) is doubled substantially, a bright observation image can be generated and displayed with few noises. Therefore, the endoscope system 10 can present an observation image in which it is easy to discover lesions, even in case a doctor moves the distal portion 24 away from the observation object to search for lesions.

On the other hand, in case the imaging distance is less than the threshold value (S12: NO), the light source controller 32 increases light emission of the B-LED 33 from the balanced light emission (the ratio of light quantity) of the B-LED 33, G-LED 34 and R-LED 35 of the reference white light used as the illumination light, and controls quantity of the illumination light to the quantity based on the exposure setting value (S17: light source controlling step). In this way, a white light having the optical spectrum with blue light component increased from the reference white light is irradiated on the observation object as the illumination light.

In this way, in case the observation object is imaged under the illumination light with increased blue light component, a signal value of the W pixel of the image sensor 48 becomes close to a signal value of the B pixel, because the received amount of blue light becomes larger than the case of imaging the observation object under the reference white light. Therefore, the demosaic processor 76 generates a signal of a deficient color of the each pixel by the second demosaic process which considers the W pixel to be the B pixel (S18). Then the display image signals are generated (S15) based on the image signals to which the second demosaic process was applied, and the observation image is displayed on the monitor 18 (S16).

As described above, in case the imaging distance is short, by increasing the blue light component of the illumination light and applying the second demosaic process which considers the W pixel to be the B pixel to generate and display the observation image, the same effect as in case the W pixel of the image sensor 48 is the B pixel from the beginning is obtained. In other words, it is similar to imaging the observation object with an image sensor where the number of B pixels is twice those of the G pixels and the R pixels, so the blue apparent resolution improves. Since the blue wavelength band is a wavelength band with particularly much absorptivity with the hemoglobin, the presence and density of hemoglobin clearly appear with contrast. Accordingly, in the observation image with improved blue resolution, it is easy to observe a structure such as a vascular running pattern or a pit pattern of the observation object. Therefore, the endoscope system 10 can automatically present an observation image where a structure that a doctor wishes for observation appears clearly, in case the doctor brings the distal portion 24 close to the observation object (the imaging distance shortens) to observe vascular running patterns and so on in detail.

Note that the above-described observation process, in which the green light or the blue light of the illumination light is increased depending on the imaging distance, is performed repeatedly until the observation with the endoscope system 10 is finished (S19).

In the above embodiment, in case the imaging distance is short, the illumination light with increased blue light from the reference white light is irradiated to the observation object. However, as illustrated in FIG. 1B, it is especially preferable to use illumination light with increased blue light and decreased green light. In this case, since a signal value of the W pixel becomes more close to a signal value of the B pixel, the resolution of such as vascular run patterns improves more.

Figure 19:
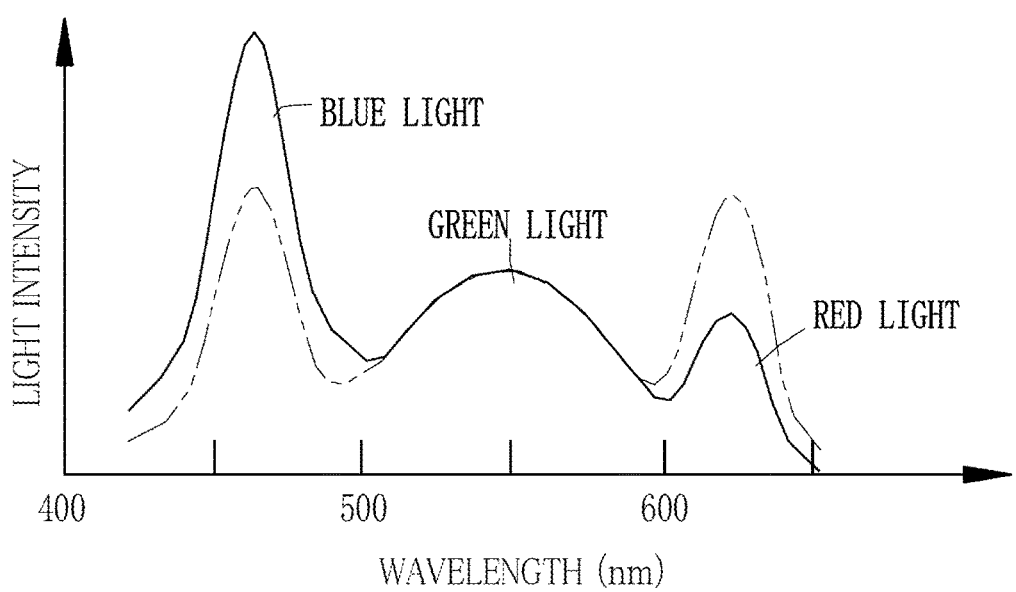
FIG. 19 is a graph illustrating an optical spectrum of illumination light in which a component of blue light is increased and a component of red light is decreased from the reference white light.

In addition, as illustrated in FIG. 19, in case the imaging distance is short and the blue light of the illumination light is increased, it is further preferable to decrease red light from the reference white light. This is because the information such as vascular run patterns is almost not included in reflected light of red light. By using the illumination light with increased blue light and decreased red light, the resolution of such as vascular run patterns improves more, since a signal value of the W pixel becomes more close to a signal value of the B pixel.

Figure 20:
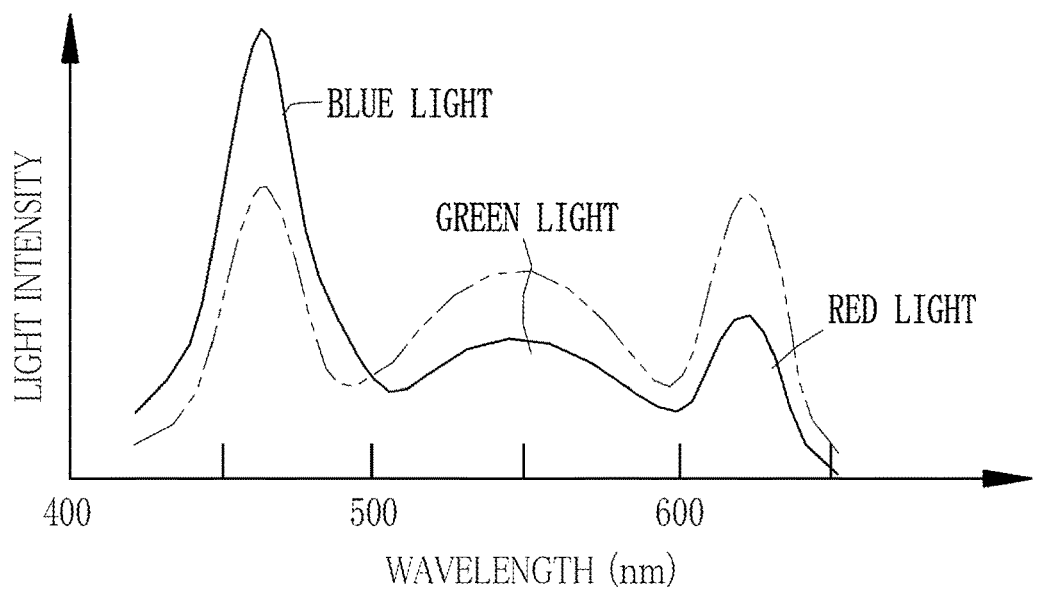
FIG. 20 is a graph illustrating an optical spectrum of illumination light in which a component of blue light is increased and components of green and red light are decreased from the reference white light.
Figure 21:
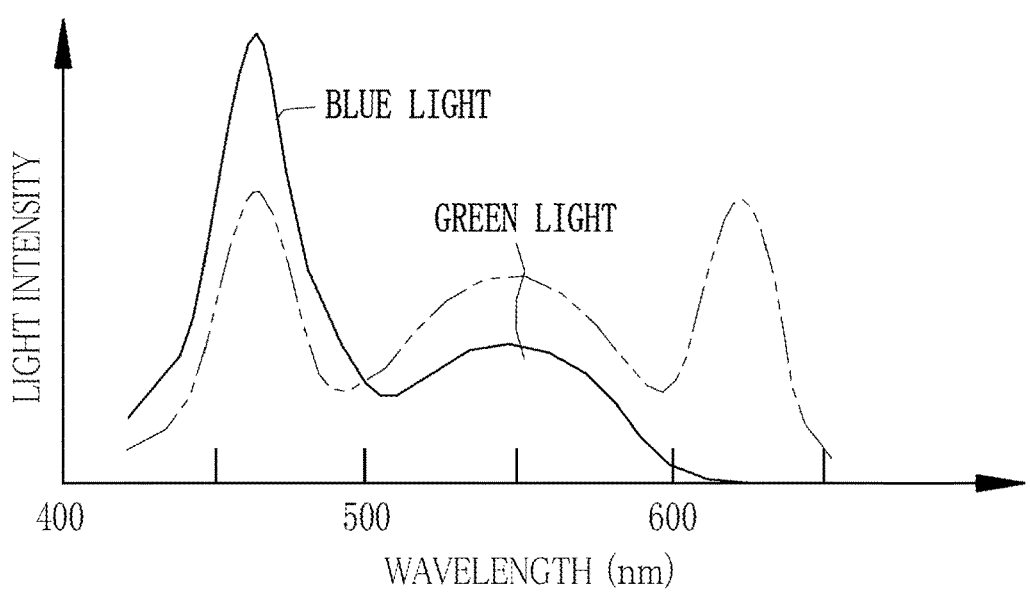
FIG. 21 is a graph illustrating an optical spectrum of illumination light in case an R-LED is turned off.

In addition, as illustrated in FIG. 20, in case the imaging distance is short and the blue light of the illumination light is increased, it is further preferable to decrease green light and red light from the reference white light. In addition, as illustrated in FIG. 21, by turning off the R-LED 35, illumination light that does not include red light can be used in case the imaging distance is short. In FIG. 21, it is illustrated the optical spectrum of the illumination light, in which blue light is increased and green light is decreased from the reference white light, and red light is not included. However, even in case green light at the same level with the reference white light is included, the resolution of such as vascular run patterns improves by turning the R-LED 35 off.

Note that in the above embodiment, the imaging distance calculator 65 calculates the imaging distance based on the exposure setting value. However, imaging distance calculator 65 may calculate the imaging distance based on a gain when the image signal is obtained from the image sensor 48. In this case, for example, the imaging distance calculator 65 acquires a gain of the automatic gain control from the CDS/AGC circuit 51. In the automatic gain control to be performed in the CDS/AGC circuit 51, a gain will be increased in case a signal value of the image signal output from the image sensor 48 becomes smaller, and a gain will be decreased in case a signal value of the image signal becomes larger. Therefore, in case the imaging distance shortens and reflected light of the illumination light incident on the image sensor 48 increases, the gain of the CDS/AGC circuit 51 becomes smaller. On the other hand, in case the imaging distance lengthens and reflected light of the illumination light incident on the image sensor 48 decreases, the gain of the CDS/AGC circuit 51 becomes larger.

Therefore, the imaging distance calculator 65 can calculate the imaging distance from the gain of CDS/AGC circuit 51, for example by providing a table that correlates an imaging distance with a gain of the CDS/AGC circuit 51. The content of the table that correlates an imaging distance with a gain of the CDS/AGC circuit 51 may be predetermined for example based on experiments. In this way, by calculating the imaging distance based on the gain of the CDS/AGC circuit 51, the accurate imaging distance can be obtained even in case the amount of the illumination light becomes the maximum light amount that can be realized in the LED light source unit 31. Of course, both the exposure setting value and the gain of the CDS/AGC circuit 51 may be obtained so that more accurate imaging distance can be calculated based on these.

In addition, in the above embodiment, the imaging distance calculator 65 calculates the imaging distance based on the exposure setting value. However, the imaging distance can be calculated based on an imaging magnification of the imaging optical system 24b. In this case, the imaging distance calculator 65 acquires, for example, control signal indicating the position of the zooming lens 47 from the imaging optical system 24b, to calculate the imaging distance based on the position of the zooming lens 47, that is, the imaging magnification of the observation object imaged on the image sensor 48. In this way, by calculating the imaging distance based on the imaging magnification of the imaging optical system 24b, the substantial imaging distance can be precisely calculated even in case a zoom operation is made without changing a distance between the distal portion 24 and the observation object. In addition, in this modification, the control signal indicating the position of the zooming lens 47 is obtained from the imaging optical system 24b. However, control signal to make position control of the zooming lens 47 may be obtained from the zoom control unit 22b to calculate the imaging distance. In addition, the imaging distance may be calculated based on the exposure setting value and the imaging magnification, or based on the exposure setting value, the imaging magnification and the gain of the CDS/AGC circuit 51.

Figure 22:
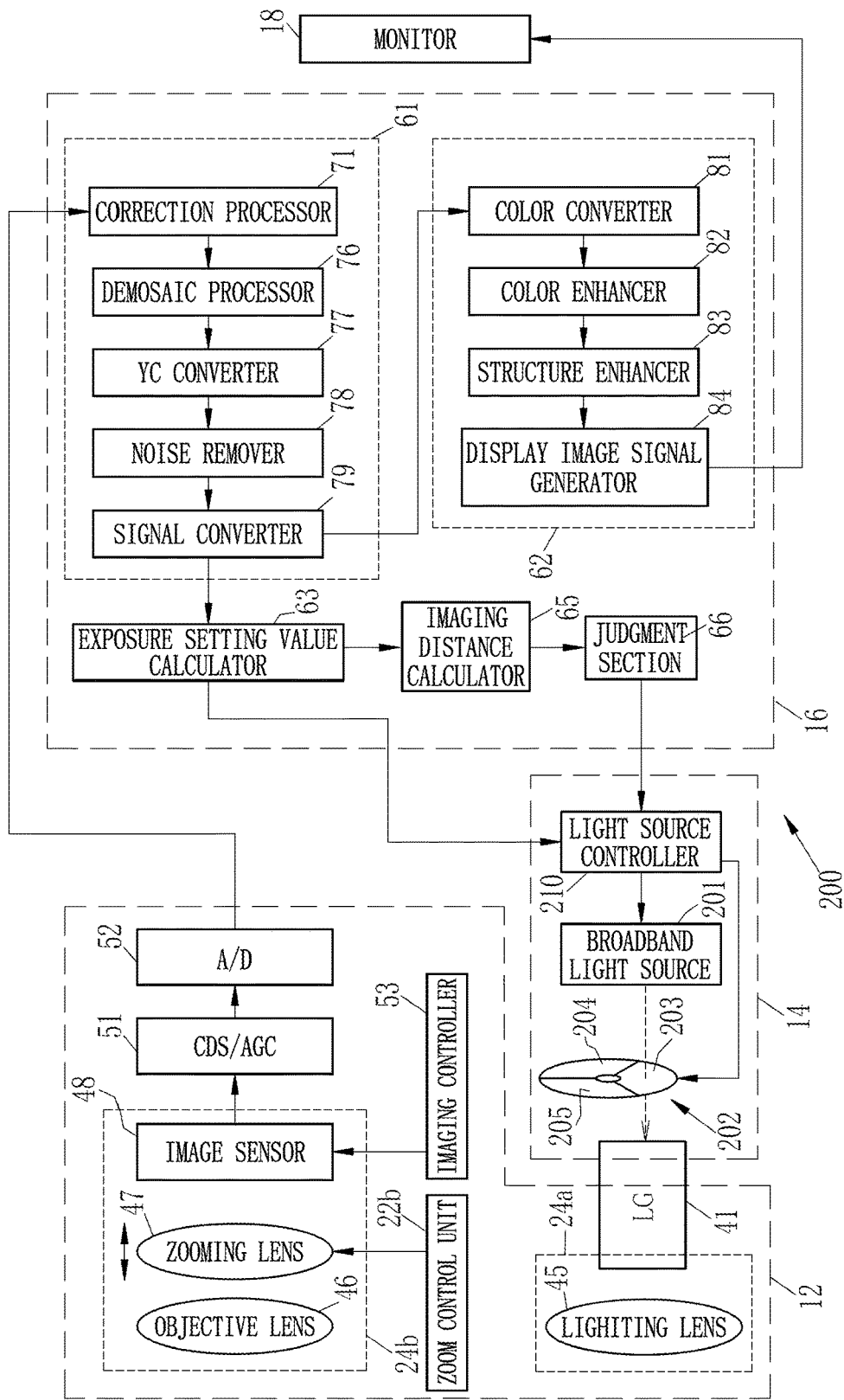
FIG. 22 is a block diagram illustrating a configuration of an endoscope system which generates illumination light with using a broadband light source and a rotary filter.

In addition, in the above embodiment, the light source device 14 produces illumination light by the LEDs 33, 34, 35 of each BGR color. However, the illumination light can be produced from a light source except the LED. For example, like an endoscope system 200 illustrated in FIG. 22, the light source device 14 may comprise a broadband light source 201 which produces white light (for example a halogen bulb or a white LED) and a rotary filter 202 which makes illumination light by limiting a wavelength band of the white light from the broadband light source 201, instead of the LED light source unit 31 and the light source controller 32. In the endoscope system 200, the broadband light source 201 and the rotary filter 202 constitute the light source unit.

The rotary filter 202 includes for example a B filter 203 for transmitting blue light, a G filter 204 for transmitting green light and an R filter 205 for transmitting red light. In addition, the rotary filter 202 is rotatably provided so that one of the filters 203, 204, 205 of each color is located on the optical path of the white light from the broadband light source 201. The rotary filter 202 is rotated in accord with a timing of imaging by the image sensor 48. Therefore, one of the blue light, green light, and red light is irradiated to the observation object.

The light source controller 210 controls a light quantity of each of blue light, green light and red light by controlling a quantity of the white light from the broadband light source 201 in sync with rotation timing of the rotary filter 202 based on the exposure setting value. In addition, the light source controller 210 controls the ratio of light quantities of blue light, green light, and red light based on the imaging distance. The control of the ratio of light quantities is substantially the same as the control of the optical spectrum of the illumination light of the above embodiment. In other words, the control of the optical spectrum of the illumination light as used in the present invention includes the control of the ratio of light quantities in case the observation object is irradiated with blue light, green light and red light sequentially.

In the endoscope system 200, the W pixel of the image sensor 48 outputs the same signal value as the case that the B pixel is used for imaging when the observation object is imaged at the timing of irradiation of blue light, and outputs the same signal value as the case that the G pixel is used for imaging when the observation object is imaged at the timing of irradiation of green light. In the same manner, the W pixel outputs the same signal value as the case that the R pixel is used for imaging when the observation object is imaged at the timing of irradiation of red light. In other words, in the endoscope system 200, the W pixel can obtain image signals of each BGR color from the beginning, and the B pixel, G pixel and R pixel can obtain a lacked image signal through the demosaic process same as the above embodiment.

In the above embodiment and the modification, the LEDs 33, 34 and 35 are used to produce illumination light. However, illumination light may be generated by using an LD (laser diode) and a fluorescent substance that emits fluorescence by receiving the laser beam from the LD, instead of the LED. In this case, the LD or the combination of the LD and the fluorescent substance constitutes the light source unit.

In addition, in the above embodiment and the modification, the light source controllers 32 and 210 are established in the light source device 14. However, the light source controllers 32 and 210 may be established in the processor device 16.

In the above embodiment, the light source controller 32 compares the imaging distance with the threshold value, and then increases either the blue light or the green light of the illumination light. However, the light source controller 32 may predetermine a first threshold value and a second threshold value (the second threshold value is higher than the first threshold value), increase the blue light of the illumination light in case the imaging distance is no more than the first threshold value, increase the green light of the illumination light in case the imaging distance is no less than the second threshold value, and use the reference white light as the illumination light in case the imaging distance is more than the first threshold value and less than the second threshold value.

In the above embodiment, the image sensor 48 comprises the W pixel for receiving blue light, green light and red light, in addition to the B pixel, G pixel, and R pixel. However, it may be used an image sensor having the B pixel, G pixel, and R pixel, and a fourth pixel for receiving blue light and green light. In other words, since the W pixel is handled as the B pixel or the G pixel in this invention, the W pixel is available in case it is able to receive at least blue light and green light. Therefore, a pixel receiving blue light and green light may be used in substitution for the W pixel.

In the above embodiment, the exposure setting value calculator 63 calculates the exposure setting value based on the average brightness of the image signals input from the signal converter 79. However, the exposure setting value calculator 63 may calculate the exposure setting value based on the signal value of the W pixel among the image signals input from the signal converter 79. This is true in case that an image sensor having a pixel receiving blue light and green light, in substitution for the W pixel.

In the above embodiment, the LED light source unit 31 includes the three LEDs 33, 34 and 35 of BGR colors. However, the number of the LEDs for the LED light source unit 31 is not limited. For example, the LED light source unit 31 may include an LED that emits narrow-band light of 410-415 nm wavelength of violet (hereinafter referred to as the V-LED), in addition to the LED 33, 34 and 35 of each BGR color. Since there is especially much absorption with the hemoglobin in the wavelength band of the V-LED, structures such as vascular running patterns and pit patterns can be observed more clearly by using the V-LED. To increase blue light component of the illumination light in case of comprising the V-LED, it may just increase light amount of the B-LED 33, or increase light amount of the V-LED without changing light amount of the B-LED 33. Further, it may increase light amount of both the B-LED 33 and the V-LED, for increasing blue light components of illumination light as a whole.

In addition, the present invention is useful also for an endoscope system calculating oxygen saturation of an observation object. In this case, the LED light source unit 31 may be provided with an additional LED which emits signal light to be used for calculating oxygen saturation (for example an LED which emits blue narrow-band light of approximately 473 nm wavelength), or the B-LED 33 may be used in combination with an optical filter which limits a part of wavelength band of blue light emitted from the B-LED 33, to generate signal light to be used for calculating oxygen saturation.

Figure 23:
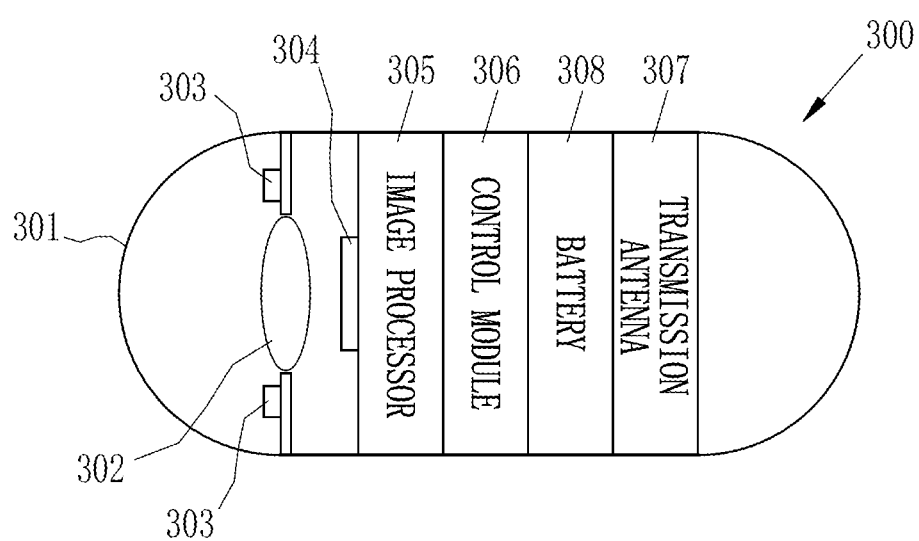
FIG. 23 is an external view of a capsule endoscope system.

In addition, the present invention can be applied to a capsule endoscope system that will be swallowed by a patient. As illustrated in FIG. 23, an capsule endoscope system 300 comprises an imaging optical system 302, an LED light source unit 303, an image sensor 304, an image processor 305, a control module 306, a transmission antenna 307 to transmit a captured image to an external device, and a battery 308 which supplies electricity to each part, in a capsule housing 301. The imaging optical system 302, the LED light source unit 303, and the image sensor 304 are constructed as same as the imaging optical system 24*b*, the LED light source unit 31, and the image sensor 48 of the endoscope system 10. The image processor 305 has the functions of the CDS/AGC circuit 51, the A/D converter 52, the image signal acquisition unit 61 and the image-processing unit 62 of the endoscope system 10. The control module 306 has the functions of the imaging controller 53, the exposure setting value calculator 63, the imaging distance calculator 65 and the light source controller 32 of the endoscope system 10.

Various changes and modifications are possible in the present invention and may be understood to be within the present invention.

What is claimed is:

1. An endoscope system comprising:
a light source device that generates illumination light to irradiate an observation object and is able to control an optical spectrum of the illumination light;
an image sensor which includes a blue pixel receiving light in a blue wavelength band, a green pixel receiving light in a green wavelength band, a red pixel receiving light in a red wavelength band, and a white pixel receiving at least light in a blue wavelength band and a green wavelength light, and images the observation object by reflected light of the illumination light from the observation object;
an imaging distance calculator which calculates an imaging distance which is a distance between the image sensor and the observation object;
a light source controller which increases a component of the blue wavelength band or the green wavelength band included in the illumination light according to the imaging distance; and
a demosaic processor configured to apply a first demosaic process performed with use of an image signal from the white pixel as a green image signal and a second demosaic process performed with use of an image signal from the white pixel as a blue image signal, the demosaic processor selectively applying the first demosaic process and the second demosaic process according to the imaging distance to an image signal which the image sensor outputs,
wherein signal value of the white pixel is used as the green image signal of the white pixel position in the first demosaic process, and is used as the blue image signal of the white pixel position in the second demosaic process, and
wherein the imaging distance calculator and the demosaic processor are implemented by a processor device.

2. The endoscope system according to claim 1, wherein the light source controller increases the component of the green wavelength band included in the illumination light as the imaging distance becomes longer and keeps the component of other wavelength bands in the illumination light at a fixed intensity level.

3. The endoscope system according to claim 1, wherein the light source controller increases the component of the blue wavelength band included in the illumination light as the imaging distance becomes shorter and keeps the component of other wavelength bands in the illumination light at a fixed intensity level.

4. The endoscope system according to claim 3, wherein the light source controller decreases the component of the green wavelength band included in the illumination light as the imaging distance becomes shorter and keeps the component of other wavelength bands in the illumination light at a fixed intensity level.

5. The endoscope system according to claim 3, wherein the light source controller decreases the component of the red wavelength band included in the illumination light as the imaging distance becomes shorter and keeps the component of other wavelength bands in the illumination light at a fixed intensity level.

6. The endoscope system according to claim 1, further comprising a judgment section which compares the imaging distance with a predetermined threshold value, judges that the imaging distance is short in case the imaging distance is shorter than the threshold value, and judges that the imaging distance is long in case the imaging distance is longer than the threshold value,
wherein
in case the judgment section judges that the imaging distance is long, the light source controller increases the component of the green wavelength band included in the illumination light, and the demosaic processor applies the first demosaic process to the image signal output from the image sensor, and
in case the judgment section judges that the imaging distance is short, the light source controller increases the component of the blue wavelength band included in the illumination light, and the demosaic processor applies the second demosaic process to the image signal output from the image sensor.

7. The endoscope system according to claim 1, further comprising an exposure setting value calculator which calculates an exposure setting value to control an exposure amount when the observation object is imaged, based on image signals which the image sensor outputs,
    wherein the imaging distance calculator calculates the imaging distance based on the exposure setting value.

8. The endoscope system according to claim 1, further comprising a gain controller that controls a gain when the image sensor outputs image signals,
    wherein the imaging distance calculator calculates the imaging distance based on the gain.

9. The endoscope system according to claim 1, further comprising an imaging optical system in which an imaging magnification is variable,
    wherein the imaging distance calculator calculates the imaging distance based on the imaging magnification.

10. A method for operating an endoscope system which includes a light source device which generates illumination light to irradiate an observation object and is able to control an optical spectrum of the illumination light, and an image sensor which has a blue pixel receiving light in a blue wavelength band, a green pixel receiving light in a green wavelength band, a red pixel receiving light in a red wavelength band, and a white pixel receiving at least light in a blue wavelength band and a green wavelength light, and images the observation object by reflected light of the illumination light from the observation object, the method comprising:
    an imaging distance calculation step in which an imaging distance calculator calculates an imaging distance which is a distance between the image sensor and the observation object;
    a source-controlling step in which a light source controller increases a component of the blue wavelength band or the green wavelength band included in the illumination light based on the imaging distance; and
    a demosaic process step in which a demosaic processor applies a first demosaic process performed with use of an image signal from the white pixel as a green image signal and a second demosaic process performed with use of an image signal from the white pixel as a blue image signal, the demosaic processor selectively applying the first demosaic process and the second demosaic process according to the imaging distance to an image signal which the image sensor outputs,
    wherein signal value of the white pixel is used as the green image signal of the white pixel position in the first demosaic process, and is used as the blue image signal of the white pixel position in the second demosaic process, and
    wherein the imaging distance calculator and the demosaic processor are implemented by a processor device.

11. A processor device being used for an endoscope system which includes a light source device which generates illumination light to irradiate an observation object and is able to control an optical spectrum of the illumination light, and an image sensor which has a blue pixel receiving light in a blue wavelength band, a green pixel receiving light in a green wavelength band, a red pixel receiving light in a red wavelength band, and a white pixel receiving at least light in a blue wavelength band and a green wavelength light, and images the observation object by reflected light of the illumination light from the observation object, the light source device including a light source controller that increases a component of the blue wavelength band or the green wavelength band included in the illumination light based on an imaging distance, the processor device comprising:
    an imaging distance calculator which calculates an imaging distance which is a distance between the image sensor and the observation object;
    a demosaic processor configured to apply a first demosaic process performed with use of an image signal from the white pixel as a green image signal and a second demosaic process performed with use of an image signal from the white pixel as a blue image signal, the demosaic processor selectively applying the first demosaic process and the second demosaic process according to the imaging distance to an image signal which the image sensor outputs,
    wherein signal value of the white pixel is used as the green image signal of the white pixel position in the first demosaic process, and is used as the blue image signal of the white pixel position in the second demosaic process.

12. The endoscope system according to claim 1, wherein the light source device includes the light source controller and a light source unit which generates the illumination light to irradiate the observation object and is able to control an optical spectrum of the illumination light, and wherein the light source controller controls the light source unit.

13. The method for operating an endoscope system according to claim 10, wherein the light source controlling step is performed by the light source controller included in the light source device which controls the light source unit included in the light source device and generates the illumination light to irradiate the observation object.

* * * * *